United States Patent [19]

Schroeder et al.

[11] 4,184,982

[45] Jan. 22, 1980

[54] PREPARATION OF A SILICATE HYDROGENATION CATALYST

[75] Inventors: Wolfgang Schroeder, Bad Durkheim; Wolfgang Franzischka, Ludwigshafen, both of Fed. Rep. of Germany

[73] Assignee: BASF Aktiengesellschaft

[21] Appl. No.: 915,011

[22] Filed: Jun. 13, 1978

[30] Foreign Application Priority Data

Jun. 14, 1977 [DE] Fed. Rep. of Germany ....... 2726720

[51] Int. Cl.$^2$ .................... B01J 37/02; B01J 29/00; B01J 29/10
[52] U.S. Cl. .................... 252/452; 252/454; 252/459
[58] Field of Search .................... 252/452, 454, 459

[56] References Cited

U.S. PATENT DOCUMENTS

| | | | |
|---|---|---|---|
| 2,034,077 | 3/1936 | Arnold et al. | 252/454 |
| 2,040,233 | 5/1936 | Adkins | 252/454 |
| 2,392,107 | 1/1946 | Teter | 252/452 |
| 2,716,665 | 8/1955 | Hadley et al. | 252/454 |
| 3,551,352 | 12/1970 | Carr et al. | 252/452 |

Primary Examiner—Carl F. Dees
Attorney, Agent, or Firm—Keil & Witherspoon

[57] ABSTRACT

A hydrogenation catalyst containing copper, nickel or cobalt as the active metal is obtained by precipitating the metal salt solution with an alkali metal silicate solution containing excess alkali, and drying and reducing the resulting precipitate.

11 Claims, No Drawings

PREPARATION OF A SILICATE HYDROGENATION CATALYST

It is known to prepare hydrogenation catalysts in which the active compound is finely dispersed in alumina by precipitating the compound which possesses the hydrogenating action from a solution which also contains dissolved aluminum salts by means of an alkali metal carbonate solution and carrying out the precipitation under conditions intended to produce the crystal structure of manasseite in one case, and the crystal structure of tacovite in another process (cf. British Pat. No. 1,342,020 and U.S. Pat. No. 4,009,124).

In another case, the precipitation gives a nickel-/alumina catalyst having an amorphous structure.

In catalyst systems which contain silica instead of alumina as the carrier or as the chemically inert medium in which the active compound is dispersed, the methods hitherto used to try to achieve fine dispersion of the active compounds has been either to impregnate a porous carrier with a solution of the compounds or to suspend the finely divided carrier in a solution and precipitate the compounds onto it. Methods for the coprecipitation of the active component and of the inert material have also been disclosed.

We have found that a catalyst obtained by coprecipitation of copper, nickel and/or cobalt and silica and having a metal content of from about 40 to 80% by weight, based on the total weight of the molded, dried, heat-treated and reduced solid, exhibits a distinct activity maximum, which is pronounced at a metal content of from about 60 to 70%, some fluctuations being observed depending on the nature of the metal. Accordingly, the invention relates to a process for the preparation of a hydrogenation catalyst which contains copper, nickel or cobalt on a silica carrier, wherein an aqueous solution of a salt of copper, nickel and/or cobalt is mixed with an alkali metal silicate solution, containing excess alkali metal hydroxide, in such amount that the mixture reacts approximately neutral and the weight ratio of copper, nickel and/or cobalt to silica in the finished catalyst is from 0.5 to 2, and, using conventional methods, the precipitate formed on mixing is isolated, molded, dried and treated with a reducing agent.

Specifically, we have found activity maxima at the following metal concentrations:
for copper, from 50 to 80, especially from 60 to 65, % by weight,
for nickel, from 50 to 80, especially from 65 to 70, % by weight,
for cobalt, from 55 to 75, especially 65% by weight.

The catalysts are prepared in accordance with a principle which is the same for all the metals. The preferred metal salt is a compound free from chlorine and sulfur, eg. the nitrate, acetate or formate. It is converted to an aqueous solution which is preferably from about 1 to 3 molar.

Commercial waterglass (alkali metal silicate solution) can be used as the starting material for the preparation of the catalyst. This waterglass can exhibit various alkali metal oxide/$SiO_2$ ratios; the molar ratio $Me_2O/SiO_2$ may be, for example, from 0.25 to 1.4. Accordingly, these compounds as a rule do not have a stoichiometric composition, though as a rule the molar ratio is about 1, corresponding to the metasilicate. It is true that silicates richer in alkali metal can be prepared but with increasing alkali metal content there is an increasing tendency to undergo hydrolysis in aqueous solution, so that such compounds can hardly be regarded as defined compounds which are stable for a lengthy period. Silicates richer in $SiO_2$ contain polymeric silicic acid anions, as is known to be the case for conventional waterglass (cf. Hollemann-Wiberg, Lehrbuch der anorg. Chemie).

We have found that for the purposes of the invention such stable polysilicate anions are the best starting point. Accordingly, the starting material used is a waterglass with a molar ratio $Me_2O:SiO_2$ of, for example, from 0.5 to 1, to which waterglass an alkali metal hydroxide (Me=Na or K) is added. An excess of alkali metal hydroxide means the amount of alkali metal hydroxide by which the calculated molar ratio $Me_2O:SiO_2$ is raised to above 1. Accordingly the solution thus obtained contains silicate ions and excess alkali metal. The concentration of silicate ions is not critical.

The alkali metal silicate solution and the metal salt solution are combined in amounts which, taking due account of the concentration, result in the desired ratio, the combination preferably being carried out at an elevated temperature, eg. at from 60° to 90° C. Whilst bringing the two solutions together, a pH of from 6 to 8, preferably of about 7, is maintained in the resulting mixture. The amount of alkali metal hydroxide required for this purpose is in each case determined by a preliminary experiment.

After the precipitation, the precipitate is washed free from alkali and from nitrate and is then separated from the wash water.

The precipitate is dried under gentle conditions, either by drying under reduced pressure at from 100° to 120° C., or by spray-drying at from 100° to 150° C.

Spray-drying gives the dried catalyst intermediate in a particle size suitable for hydrogenation by the suspension process. The product from either method of drying can be used for tableting or molding into other shapes suitable for fixed bed hydrogenation.

EXAMPLE 1

To prepare solution 1, hydrated copper-(II) nitrate ($Cu(NO_3)_2.3H_2O$) was dissolved in water to give a 1-molar solution.

To prepare solution 2, commercial potassium waterglass containing 4.45 moles of $SiO_2$ per kilogram and 1.52 moles of $K_2O$ per kilogram was used in an amount which provided 0.67 mole of $SiO_2$ per mole of copper dissolved in solution 1. Accordingly, 150 g of potassium waterglass was used per liter of solution 1. This waterglass does not contain sufficient $K_2O$ to bind the nitrate ions so that KOH had to be added to the waterglass in an amount of 1.544 moles of KOH per liter of solution 1. Per liter of solution 1, solution 2 thus contained, as the precipitation equivalent, 0.67 mole of $SiO_2$ and 1 mole of $K_2O$ (=2 moles of KOH). Finally, solution 2 was brought to a volume corresponding to solution 1, in order to be able to carry out the precipitation conveniently.

The two solutions were fed in the ratio of 1:1 into a kettle equipped with an efficient stirrer. A temperature of 80°–90° C. was maintained in the stirred kettle by external heating and by preheating the solutions. Whilst bringing the solutions together, a pH of 7 was maintained in the mother liquor by regulating the amount of solution 1 run in.

After completion of precipitation, the pure blue precipitate was separated from the mother liquor and then washed with cold water until nitrate was no longer detectable in the wash water.

The precipitate was mechanically separated from the wash water and then dried in a reduced pressure drying oven at an air temperature of about 120° C.

At this stage the dry material had a pastel blue color. After subsequent heating at 300° C., the dry material had a pure green hue and X-ray analysis indicated that the material was amorphous. Part of this dry material was mechanically brought to a particle size of from 60 to 100 μm, which is a suitable size for carrying out suspension catalysis experiments. Another part was molded to give cylindrical tablets with principal dimensions of 3×3 mm and was then heated at 350° C. In this tablet form, the catalyst intermediate is suitable for fixed bed experiments.

The copper concentration in the reduced material was 62% by weight. Further catalysts were prepared by following the same general method of preparation; their composition is shown in the Examples which follow.

| Example No. | Composition | % by weight of the active component in the reduced catalyst | X-ray analysis |
|---|---|---|---|
| 2 | $CuO \cdot 3SiO_2$ | 30 | amorphous |
| 3 | $CuO \cdot SiO_2$ | 51 | amorphous |
| 4 | $2\ CuO \cdot SiO_2$ | 68 | amorphous |
| 5 | $NiO \cdot SiO_2$ | 50 | amorphous |
| 6 | $2\ NiO \cdot SiO_2$ | 66 | amorphous |
| 7 | $4\ NiO \cdot SiO_2$ | 80 | amorphous |
| 8 | $CoO \cdot SiO_2$ | 50 | amorphous |
| 9 | $1.5\ CoO \cdot SiO_2$ | 60 | amorphous |
| 10 | $2\ CoO \cdot SiO_2$ | 66 | amorphous |
| 11 | $2.5\ CoO \cdot SiO_2$ | 71 | amorphous |
| 12 | $3\ CoO \cdot SiO_2$ | 75 | faintly detectable proportion of crystalline oxide |

USE EXAMPLE 1

The powder from Example 1, prepared for use in suspension catalysis, was heated to 120° C. in an indirectly heated fluidized bed in a stream of nitrogen. After admixture of hydrogen in an amount of from 1 to 2% by volume of the nitrogen, the reduction of the copper oxide component of the catalyst intermediate commenced. The water formed was condensed and measured. When the separation of water became slower, the temperature was raised, finally reaching 180° C. The calculated amount of water was formed. The stream of nitrogen was then shut off and the fluidized bed was charged with pure hydrogen.

After it had cooled under hydrogen, the catalyst was suspended in a mixture of methyl esters of dicarboxylic acids of 4 to 6 carbon atoms, in an amount of 5% by weight, based on the suspension. To hydrogenate the suspension, it was transferred into a heated stirred autoclave and after removing the atmospheric oxygen the autoclave was brought to the hydrogenating conditions of 230° C. and 250 bars. The progress of the hydrogenation reaction was followed by observing the hydrogen consumption and by determining the ester number on periodically removed samples.

The original ester mixture had an ester number of 700; after 12 hours, the ester number of the hydrogenated mixture was found to be 60.

COMPARATIVE EXPERIMENT 1

The procedure followed was as described in Use Example 1, except that the catalyst used was an ADKINS copper/chromium oxide catalyst as sold, for example, by Girdler-Sudchemie under the tradename G-13.

After 12 hours' hydrogenation under the conditions described in Use Example 1, the ester number was found to be 480.

USE EXAMPLE 2

The procedure followed was as described in Use Example 1, but with the catalyst obtained as described in Example 2. After 12 hours' hydrogenation, the ester number was found to be 300.

USE EXAMPLE 3

The procedure followed was as described above, but using the catalyst from Example 3. After 12 hours' hydrogenation, the ester number was found to be 200.

USE EXAMPLE 4

The procedure followed was as described in Use Example 1, except that the catalyst from Example 4 was used. After 12 hours' hydrogenation the ester number was found to be 100.

The above Use Examples show firstly the advance achieved over the prior art and secondly the special advantage of the catalyst of Example 1 over catalysts richer or poorer in copper, ie. the existence of a maximum catalytic effect.

EXAMPLE 13

To prepare solution 1, nickel nitrate ($Ni(NO_3)_2 \cdot 6H_2O$) was dissolved in water to give a 1-molar solution.

To prepare solution 2, the waterglass described in Example 1 was used, in an amount corresponding to 0.5 mole of $SiO_2$ per mole of nickel dissolved in solution 1. Accordingly, 112 g of potassium waterglass were used per liter of solution 1. This waterglass does not contain sufficient $K_2O$ to bind the nitrate ions so that KOH had to be added to the waterglass in an amount of 1.66 moles of KOH per liter of solution 1. Per liter of solution 1, solution 2 thus contained, as the precipitation equivalent, 0.50 mole of $SiO_2$ and 1 mole of $K_2O$ (=2 moles of KOH).

The precipitate was prepared, and treated, as described in Example 1.

The dried precipitate was heated at 550° C. Part of this dry material was mechanically brought to a particle size of from 60 to 100 μm, which is a suitable size for carrying out suspension catalysis experiments. Another part was pressed to give cylindrical tablets 3 mm high and of 5 mm diameter. In this tablet form, the catalyst intermediate is suitable for fixed bed experiments.

USE EXAMPLE 5

The powder from Example 13, prepared for suspension catalysis, was heated stepwise to 570° C. in an indirectly heated fluidized bed with circulating hydrogen, and was thereby reduced.

After it had cooled, the catalyst was suspended in a technical-grade crude butynediol solution to give a suspension containing 5% by weight of catalyst. According to analysis by gas chromatography, the crude butynediol solution had the following composition:
water: 60.3% by weight butynediol: 38.3% by weight
propynol: 0.5% by weight
formaldehyde: 0.3% by weight
others: 0.6% by weight The catalyst suspension was transferred into a high pressure bubble column and was treated with hydrogen at 90 bars and 40°–50° C. The flow rate of the hydrogen in the bubble column (assumed empty) was 2 cm/sec. At intervals of 10 minutes, samples were taken from the bubble column and analyzed. The end of the hydrogenation reaction was defined as the point at which the concentration of the hydroxybutyraldehyde formed as an intermediate fell to below 0.5%, based on the anhydrous solution; at this stage, carbon-carbon multiple bonds are no longer detectable. This end of the hydrogenation reaction was in each case reached after 45 minutes.

COMPARATIVE EXPERIMENT FOR USE EXAMPLE 5

If Raney nickel is used as the catalyst and in other respects the procedure described above is followed, the end of the hydrogenation is only reached after 130 minutes.

USE EXAMPLES 6 TO 8

If the procedure described above is followed but catalysts obtained according to Examples 5, 6 and 7 are used, the results shown below are found.

| Catalyst from | % by weight of Ni in the reduced catalyst | End of the hydrogenation reaction |
| --- | --- | --- |
| Example 5 | 49.5 | 60 minutes |
| Example 6 | 66 | 45 minutes |
| Example 7 | 80 | 55 minutes |

The above Use Examples show firstly the advance achieved over the prior art and secondly the special advantage of the catalyst of Example 6 over catalysts richer or poorer in nickel.

USE EXAMPLES 9 TO 12

The catalysts obtained from Examples 9 to 12, in a particle size of 60 to 100 μm, were reduced in an indirectly heated fluidized bed in a stream of hydrogen at up to a maximum of 550° C. They were then suspended in toluene and mixed with adipodinitrile in a high pressure bubble column. At that stage the mixture consisted of 76% by weight of toluene, 19% by weight of adipodinitrile and 5% by weight of catalyst. It was then hydrogenated at 90 bars and 100° C., the flow rate of hydrogen in the bubble column (assumed empty) being 2 cm/sec. The progress of the hydrogenation reaction, in which mainly hexamethylenediamine is formed, was followed from the increase in amine number with time. The results are summarized in Table 3.

| Use Example | Catalyst from | % by weight of Co in the reduced catalyst | Hourly increase in amine number |
| --- | --- | --- | --- |
| 9 | Example 9 | 60 | 14 |
| 10 | Example 10 | 66 | 42 |
| 11 | Example 11 | 71 | 20 |
| 12 | Example 12 | 75 | 10 |
| Comparison | Raney cobalt | about 90 | 17 |

The above Use Examples show firstly the advance achieved over the prior art and secondly the special advantage of the catalyst of Example 10 over catalysts richer or poorer in cobalt.

USE EXAMPLE 13

Following the general instruction of Example 13, a catalyst having the formula $CuO.CoO.SiO_2$ was prepared and was molded to give tablets 5 mm high and of 5 mm diameter. In the reduced state, the catalyst thus contained 67% by weight of active metals. 500 ml of this catalyst were introduced into a thermostatically controllable, pressure-resistant reactor. Hydrogen was passed downward through the catalyst packing in an amount corresponding to 100 liters (S.T.P.) per hour at the reactor outlet. The reactor was set to a pressure of 200 bars and to 75° C. A mixture of 1 part by volume of benzonitrile and 2 parts by volume of liquid ammonia was then run continuously into the reactor at a rate of 1.2 liters/hour. After removal of excess ammonia, the reactor effluent consisted of 98% w/w benzylamine, 0.05% w/w benzonitrile and less than 2% byproducts or impurities.

We claim:

1. A process for the preparation of a hydrogenation catalyst which contains copper, nickel or cobalt on a silica carrier, wherein an aqueous solution of a salt of copper, nickel and/or cobalt is mixed with an alkali metal silicate solution, containing excess alkali metal hydroxide, in such amount that the mixture reacts approximately neutral and the weight ratio of copper, nickel and/or cobalt to silica in the finished catalyst is from 0.5 to 2, and, using conventional methods, the precipitate formed on mixing is isolated, molded, dried and treated with a reducing agent.

2. The process of claim 1, wherein an alkali metal silicate solution is used in which the molar ratio of $Me_2O$ to $SiO_2$, where Me is potassium or sodium, is greater than 0.5.

3. The process of claim 1, wherein the aqueous salt solution is from about 1 to 3 molar.

4. The process of claim 1, wherein mixing and precipitation is carried out at from 60° to 90° C.

5. The process of claim 1, wherein the finished catalyst contains from 50 to 80% by weight of copper.

6. The process of claim 1, wherein the finished catalyst contains from 60–65% by weight of copper.

7. The process of claim 1, wherein the finished catalyst contains from 50–80% by weight of nickel.

8. The process of claim 1, wherein the finished catalyst contains from 65–70% by weight of nickel.

9. The process of claim 1, wherein the finished catalyst contains from 55–75% by weight of cobalt.

10. The process of claim 1, wherein the finished catalyst contains about 65% by weight of cobalt.

11. A catalyst as obtained by the process of any of claims 5, 6, 7, 8 or 9.

* * * * *